United States Patent
Takeshita et al.

(10) Patent No.: US 11,447,752 B2
(45) Date of Patent: Sep. 20, 2022

(54) IN VITRO MODEL FOR BLOOD-BRAIN BARRIER AND METHOD FOR PRODUCING IN VITRO MODEL FOR BLOOD-BRAIN BARRIER

(71) Applicant: Yamaguchi University, Yamaguchi (JP)

(72) Inventors: Yukio Takeshita, Ube (JP); Takashi Kanda, Ube (JP)

(73) Assignee: YAMAGUCHI UNIVERSITY, Yamaguchi (JP)

( * ) Notice: Subject to any disclaimer, the term of this patent is extended or adjusted under 35 U.S.C. 154(b) by 1017 days.

(21) Appl. No.: 16/092,328

(22) PCT Filed: Mar. 22, 2017

(86) PCT No.: PCT/JP2017/011361
§ 371 (c)(1),
(2) Date: Oct. 9, 2018

(87) PCT Pub. No.: WO2017/179375
PCT Pub. Date: Oct. 19, 2017

(65) Prior Publication Data
US 2019/0144832 A1    May 16, 2019

(30) Foreign Application Priority Data
Apr. 15, 2016   (JP) .............................. JP2016-081995

(51) Int. Cl.
| C12N 5/071 | (2010.01) |
| C12N 5/10 | (2006.01) |
| G01N 33/50 | (2006.01) |
| C12N 5/079 | (2010.01) |

(52) U.S. Cl.
CPC ........... *C12N 5/0697* (2013.01); *C12N 5/069* (2013.01); *C12N 5/0618* (2013.01); *C12N 5/0622* (2013.01); *C12N 5/10* (2013.01); *G01N 33/5058* (2013.01); *G01N 33/5064* (2013.01); *G01N 33/5082* (2013.01); *C12N 2502/08* (2013.01); *C12N 2502/086* (2013.01); *C12N 2502/28* (2013.01); *C12N 2533/90* (2013.01)

(58) Field of Classification Search
CPC .. C12N 5/0697; C12N 5/0618; C12N 5/0622; C12N 5/069; C12N 5/10; C12N 2502/08; C12N 2502/086; C12N 2502/28; C12N 2533/90; C12N 2523/00; C12N 2533/52; G01N 33/5058; G01N 33/5064; G01N 33/5082
See application file for complete search history.

(56) References Cited

U.S. PATENT DOCUMENTS
2010/0273200 A1   10/2010  Niwa et al.

FOREIGN PATENT DOCUMENTS
| JP | 2001-238681 A | 9/2001 |
| JP | 2007-166915 A | 7/2007 |

OTHER PUBLICATIONS

Kamiichi et al. "Establishment of a new conditionally immortalized cell line from human brain microvascular endothelial cells: a promising tool for human blood-brain barrier studies."Brain Res. Dec. 7, 2012; 1488:113-22. (Year: 2012).*
Ramboer et al. "Strategies for immortalization of primary hepatocytes."J Hepatol.Oct. 2014;61(4):925-43. (Year: 2014).*
Ahuja et al. "SV40 large T antigen targets multiple cellular pathways to elicit cellular transformation."Oncogene.Nov. 21, 2005;24(52):7729-45. (Year: 2005).*
Ahler et al. "Doxycycline alters metabolism and proliferation of human cell lines."PLoS One.May 31, 2013;8(5):e64561. (Year: 2013).*
Sano et al. "Establishment of a new conditionally immortalized human brain microvascular endothelial cell line retaining an in vivo blood-brain barrier function."J Cell Physiol.Nov. 2010;225(2):519-28. (Year: 2010).*
Mihajlovic et al. "Safety evaluation of conditionally immortalized cells for renal replacement therapy."Oncotarget. Sep. 3, 2019; 10(51) : 5332-5348. (Year: 2019).*
International Search Report dated Jun. 6, 2017, issued in counterpart application No. PCT/JP2017/011361 (2 pages).
Nakagawa et al., "Isolation of cells constituting the blood-brain barrier and reconstruction of the in vitro BBB model", Folia Pharmacol. Jpn., 2014, vol. 143, No. 3, pp. 137-143, cited in ISR, w/ English partial translation (19 pages).
Nakagawa et al., "1. In vitro blood-brain barrier reconstruction model (BBB Kit) and their application to the functional analysis", Japanese Journal of Cerebral Blood Flow and Metabolism, 2013, vol. 24, No. 2, pp. 71-74, cited in ISR, w/ English partial translation (11 pages).
Thomsen et al., "A Triple Culture Model of the Blood-Brain Barrier Using Porcine Brain Endothelial cells, Astrocytes and Pericytes", PLOS ONE, 2015, 10: e0134765, pp. 1-16, cited in Specification and ISR (16 pages).

(Continued)

*Primary Examiner* — Titilayo Moloye
(74) *Attorney, Agent, or Firm* — Wenderoth, Lind & Ponack, L.L.P.

(57) ABSTRACT

Disclosed is a method for producing an in vitro model for blood-brain barrier, including (a) a culturing conditionally immortalized astrocytes on one surface of a porous membrane and culturing conditionally immortalized brain pericytes on the other surface of the porous membrane, until both of the cells become a sheet; (b) culturing conditionally immortalized brain microvascular endothelial cells in a culture vessel, until the cells become a sheet; (c) peeling off the sheet of conditionally immortalized brain microvascular endothelial cells; (d) allowing the sheet of conditionally immortalized brain microvascular endothelial cells to come into contact with the sheet of conditionally immortalized brain pericytes, so that the sheets are arranged in layers; and (e) co-culturing a cell culture comprising three layers consisting of the sheet of conditionally immortalized brain microvascular endothelial cells, the sheet of conditionally immortalized brain pericytes, and the sheet of conditionally immortalized astrocytes.

4 Claims, 5 Drawing Sheets

(56) References Cited

OTHER PUBLICATIONS

Takeshita et al., "An in vitro Blood-brain barrier model combining shear stress and endothelial cell/astrocyte co-culture", J. Neurosci. Methods, 2014, vol. 232, pp. 165-172, cited in Specification and ISR (15 pages).

Takeshita et al., "A new in vitro blood-brain barrier (BBB) model incorporating tri-culturing system of BBB components", 57th Annual Meeting of the Japanese Sciety of Neurology abstract., 2016, vol. 56, p. S277, O-03-1, cited in ISR (1 page).

* cited by examiner

[Figure 1]
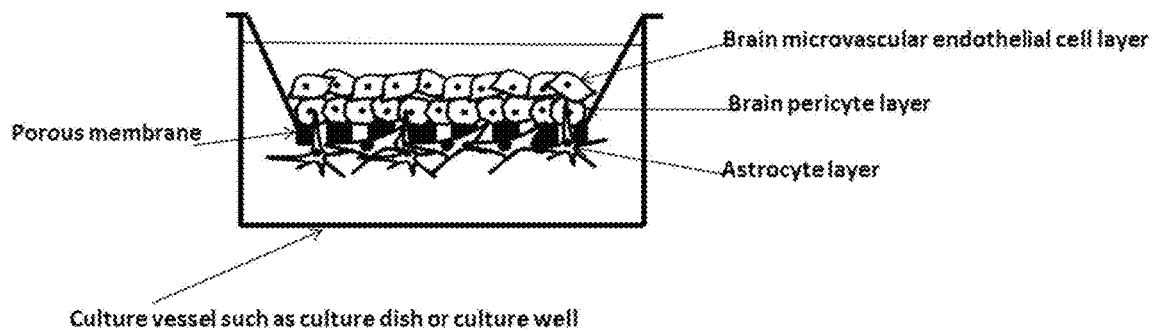
[Figure 2]
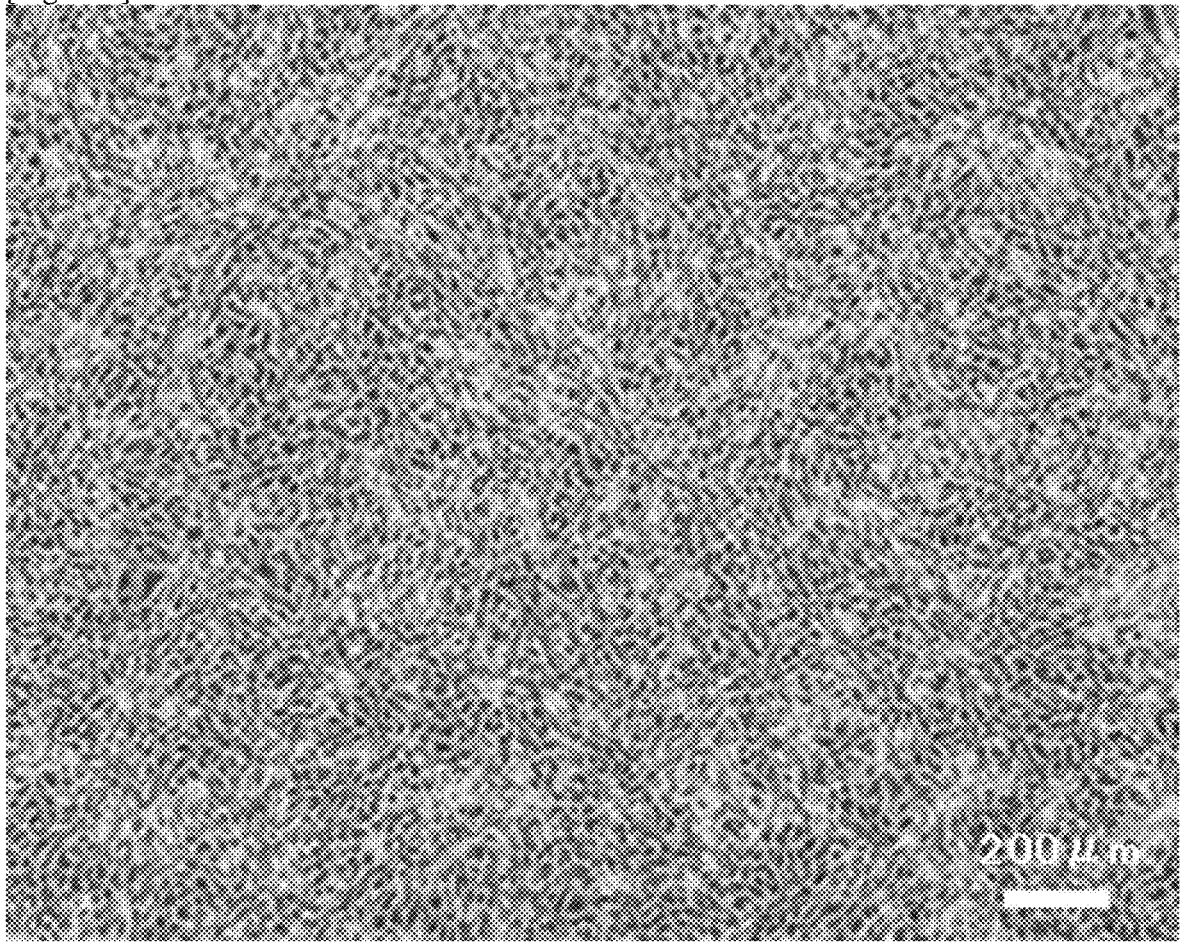

[Figure 3]
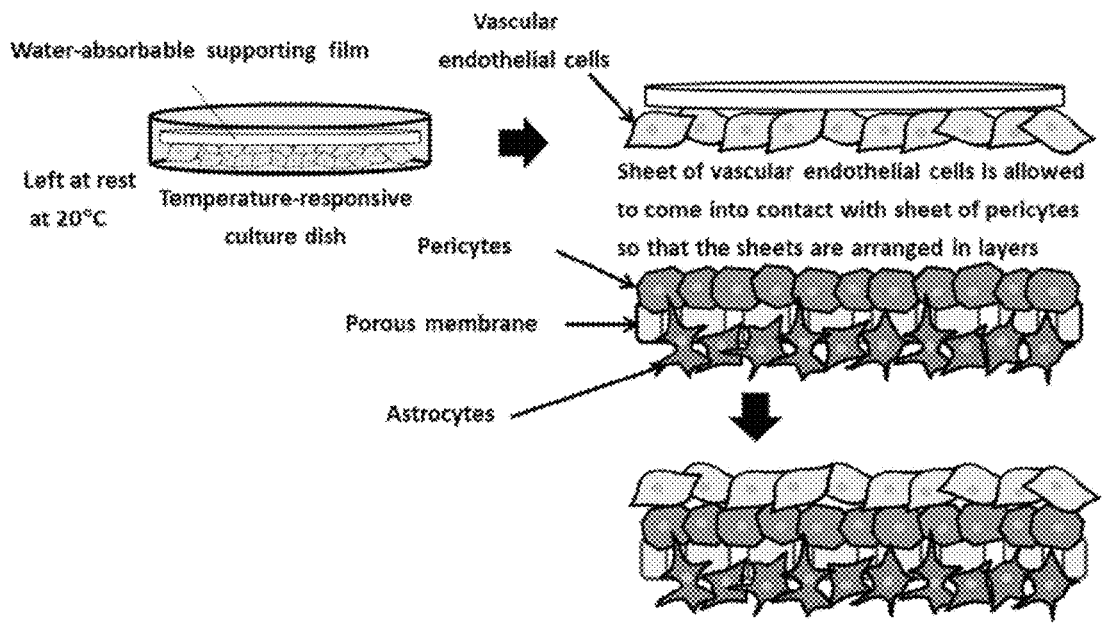
[Figure 4]
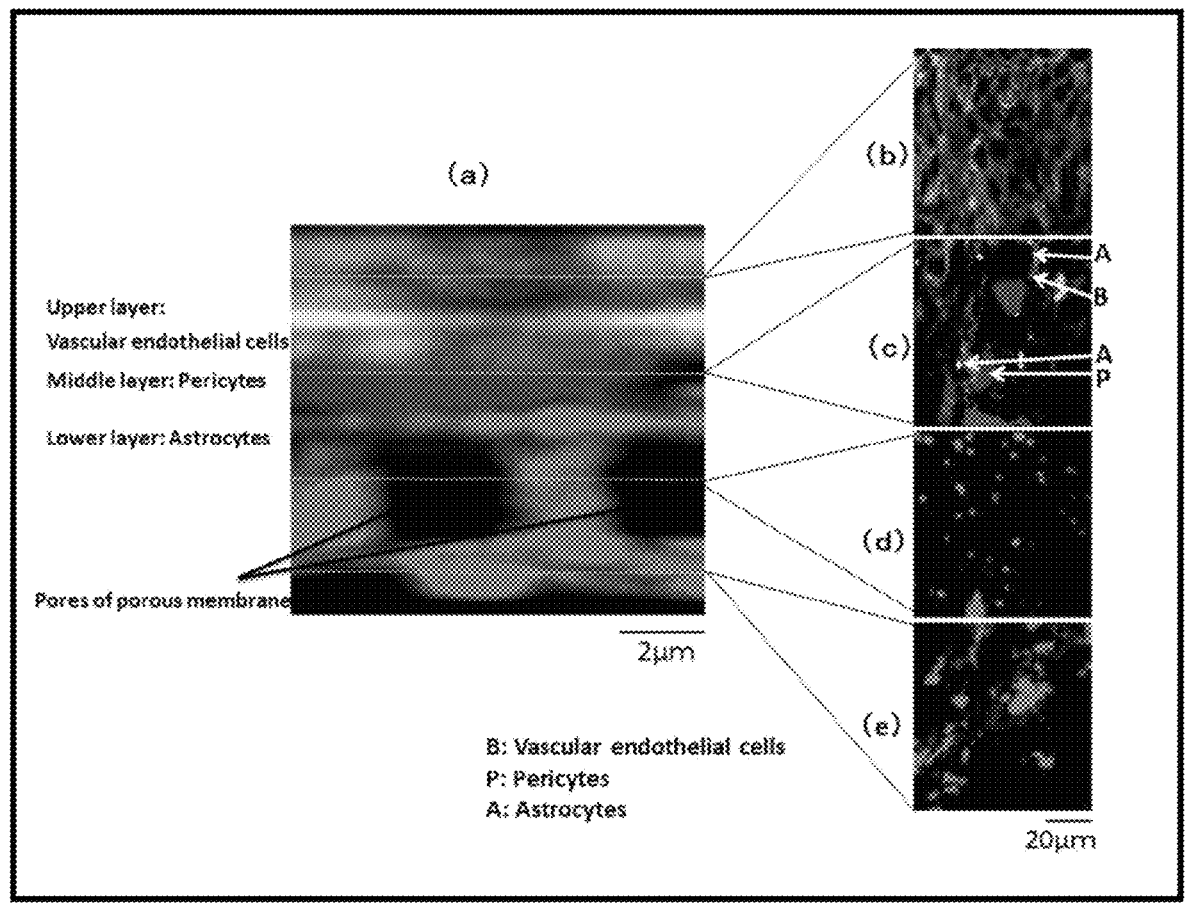

[Figure 5]
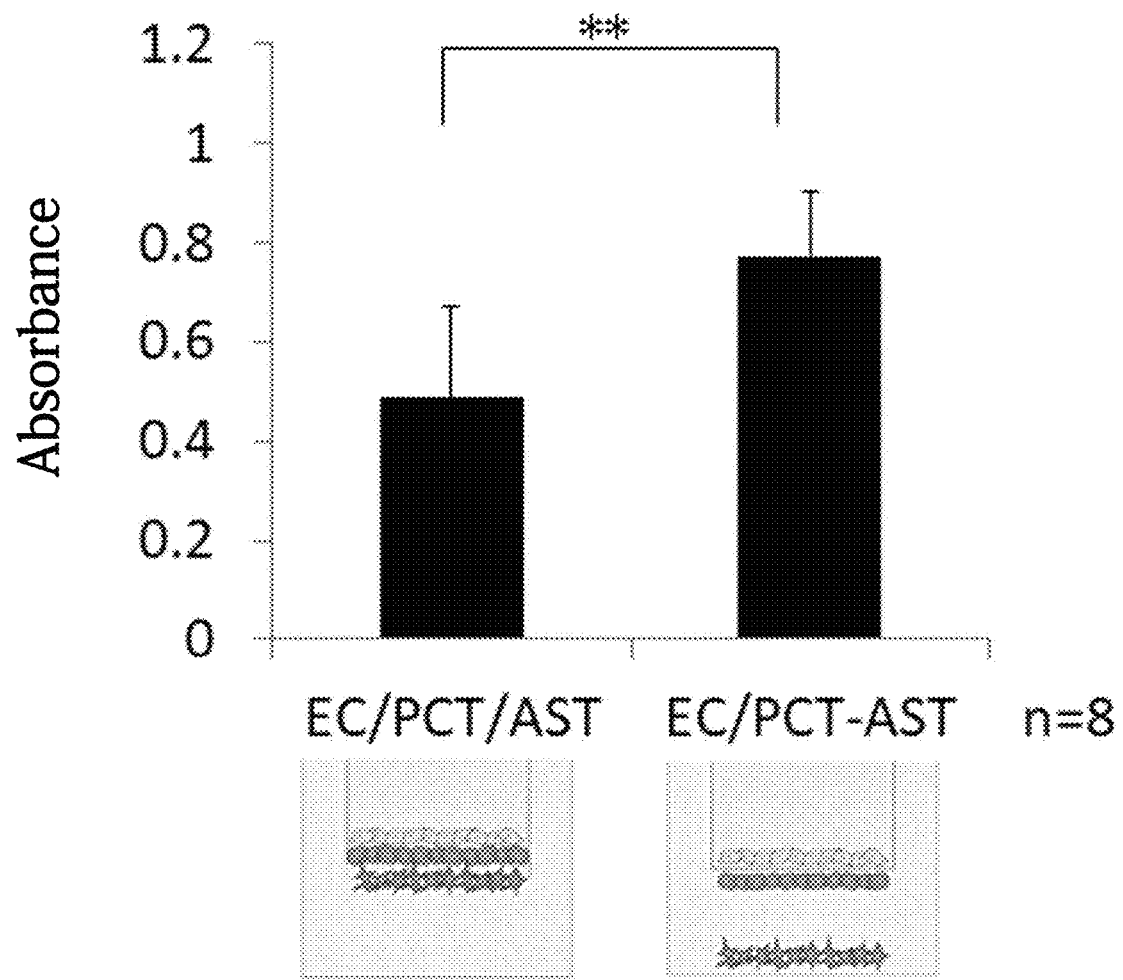

[Figure 6]
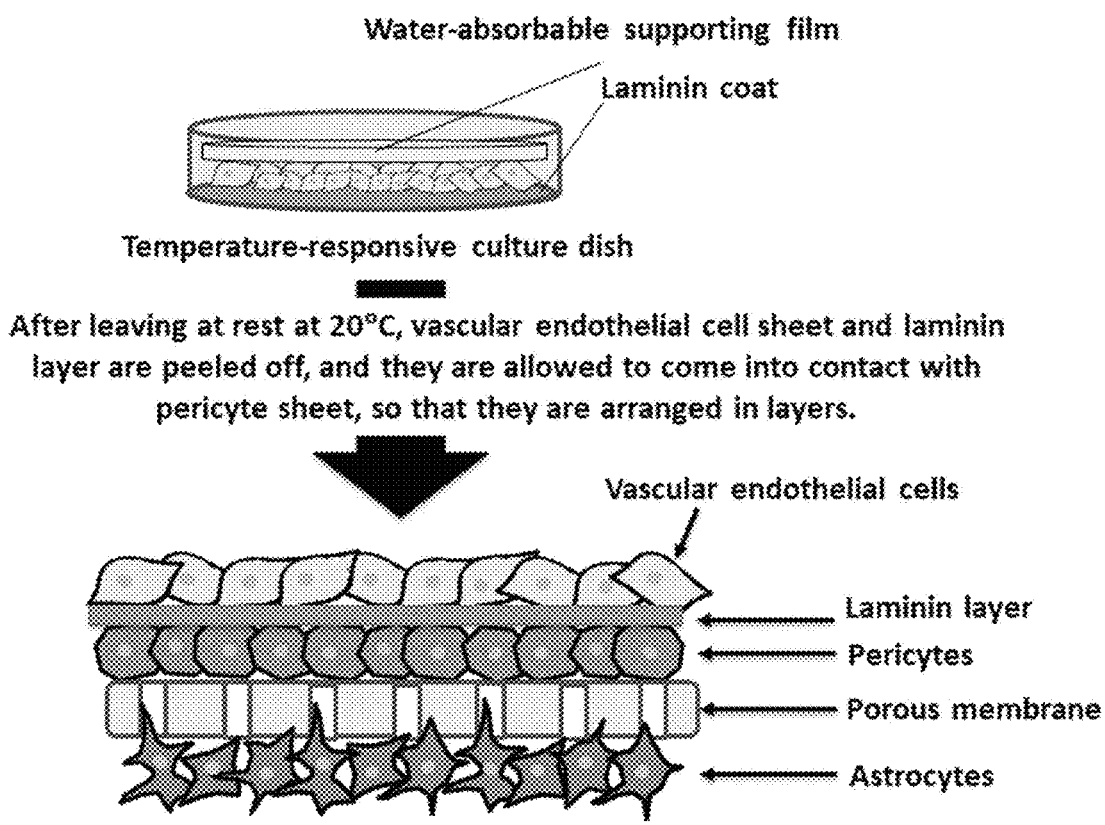

[Figure 7]
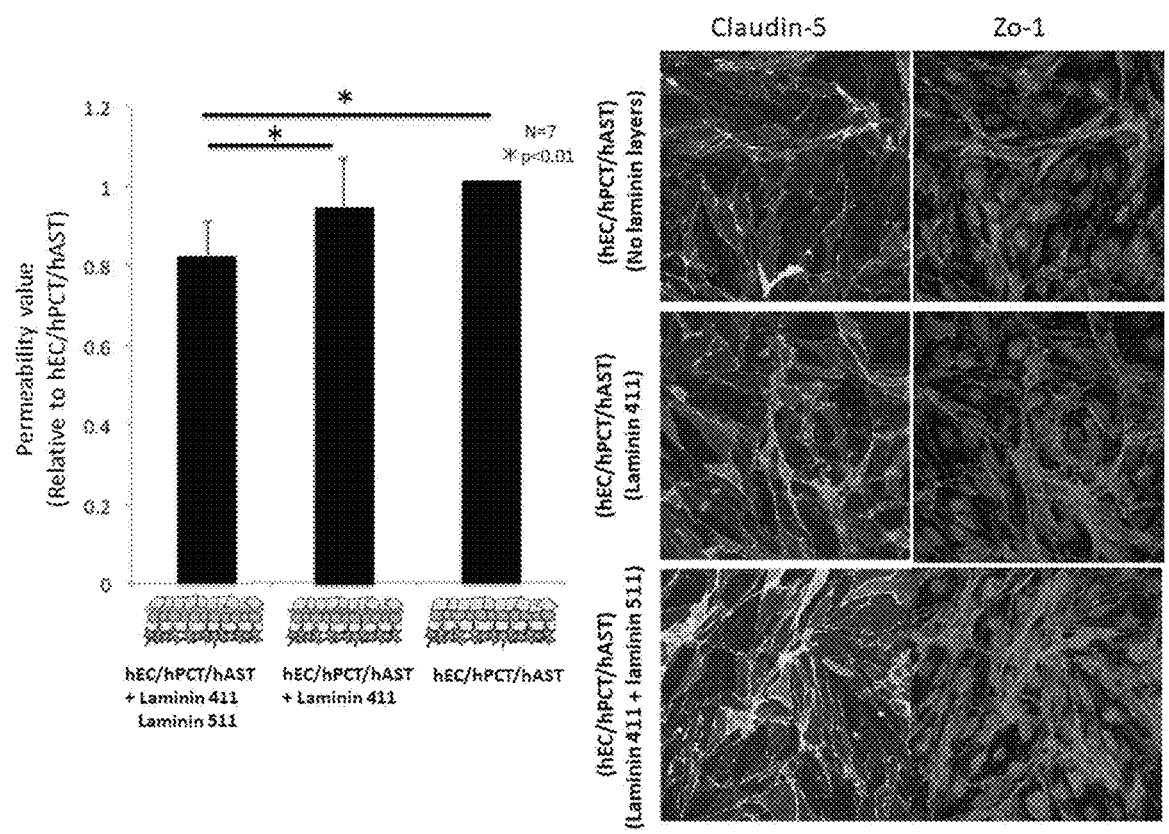

IN VITRO MODEL FOR BLOOD-BRAIN BARRIER AND METHOD FOR PRODUCING IN VITRO MODEL FOR BLOOD-BRAIN BARRIER

TECHNICAL FIELD

The present invention relates to an in vitro model for blood-brain barrier (BBB; blood-brain barrier, which is hereinafter also referred to as "BBB") and a method for producing the in vitro model for blood-brain barrier.

BACKGROUND ART

BBB plays an important role in restricting the influx of harmful substances from the outside and maintaining the internal environment of the brain. On the other hand, since BBB makes it difficult to deliver drugs to the central nervous system, there are many cases where a therapeutic agent that is effective in the periphery does not exhibit sufficient effects in the central nervous system. In addition, it has been shown that the failure of BBB is associated with the pathologic conditions of many central nervous system diseases such as Alzheimer dementia, cerebral infarction and multiple sclerosis, and thus, it is the urgent need of the day to elucidate the physiological and pathological functions of BBB. BBB is composed of three types of cells, namely, vascular endothelial cells, pericytes, and astrocytes.

To date, various BBB in vitro models had been produced using cell culture inserts.

For example, there had been reported an in vitro model for BBB, in which vascular endothelial cells are cultured on the upper surface of a cell culture insert, whereas astrocytes and pericytes are co-cultured on the upper surface of a culture well (Patent Literature 1). In the case of this model, however, the astrocytes and the pericytes are cultured in a state in which the two types of cells are mixed with each other, and the vascular endothelial cells are cultured in a state in which these cells are not allowed to come into contact with the pericytes and the astrocytes. Accordingly, it is hardly to say that this in vitro model for BBB reconstructs the structure of a blood-brain barrier in vivo.

Moreover, there had been reported a model, in which vascular endothelial cells are cultured on the upper surface of a cell culture insert, pericytes are cultured on the lower surface thereof, and astrocytes are cultured on the upper surface of a culture well (Patent Literature 2 and Non Patent Literature 1). In this model, however, since astrocytes are present on the culture well, the direct action thereof on a vascular endothelial cell layer and a pericyte layer cannot be observed, and thus, this model had been far from an ideal in vitro model that reconstructs the anatomical structure of BBB having a direct interaction of astrocytes and pericytes on vascular endothelial cells.

As a model that enables a direct contact of astrocytes with vascular endothelial cells, the present inventors had established a culture system that reflects the anatomical structure of BBB, in which a vascular endothelial cell line is cultured on the upper surface of a cell culture insert and an astrocyte cell line is cultured on the lower surface thereof, so that the foot processes of the astrocytes directly act on the vascular endothelial cell layer through the pores of the cell culture insert (Non Patent Literature 2).

As mentioned above, because of the efforts made by many researchers, a blood-brain barrier model system for reflecting an in vivo structure had been improved, but a great problem to be overcome has been still present.

When a multi-culture model for BBB is to be produced by an ordinary dispersion culture, using three types of cultured cell lines, namely, vascular endothelial cells, pericytes and astrocytes, which are main constitutional cells of BBB, since these three types of cell lines have different growth rates from one another, each cell line does not form a monolayer structure. Therefore, it had been technically difficult to construct a BBB model that reconstructs an anatomical structure, in which the three types of cells have a three-layer structure.

CITATION LIST

Patent Literature

Patent Literature 1: JP Patent Publication (Kokai) No. 2001-238681 A
Patent Literature 2: JP Patent Publication (Kokai) No. 2007-166915 A

Non Patent Literature

Non Patent Literature 1: Thomsen et al., PLOS ONE, DOI: 10.1371/journal.pone.0134765 Aug. 4, 2015
Non Patent Literature 2: Takeshita et al., J Neurosci Methods. 232, 165-172, 2014.

SUMMARY OF INVENTION

Technical Problem

Considering the aforementioned circumstances, it is an object of the present invention to construct an in vitro model that reconstructs the anatomical structure of BBB.

Solution to Problem

The present inventors have conducted intensive studies regarding a BBB model having a three-layer structure consisting of brain-derived vascular endothelial cells, pericytes and astrocytes, in which individual layers of cells can cross-talk to one another. With regard to the interaction between astrocytes and pericytes, the present inventors have found that these cells can interact with one another depending on a change in the shape of astrocytes, etc., by putting a porous membrane between these cell layers. On the other hand, with regard to the interaction between vascular endothelial cells and pericytes, the present inventors have predicted that vascular endothelial cells and pericytes could be interacted with each other by allowing the two cell layers thereof to directly come into contact with each other, and have studied about the method of contacting the two types of cells with each other. As a result of the studies, the present inventors have found that, when a cell sheet of vascular endothelial cells is produced, separately, and the produced sheet is then allowed to come into contact with a layer of pericytes, so that they are arranged in layers, the obtained model has lower material permeation properties than a conventional BBB model, and the barrier function (function to suppress permeation of materials) thereof is maintained for a long period of time, thereby successfully constructing a novel model as described above.

Therefore, the present invention includes the following (1) to (5).
(1) A method for producing an in vitro model for blood-brain barrier, comprising the following steps (a) to (e):

(a) a step of culturing conditionally immortalized astrocytes on one surface of a porous membrane and culturing conditionally immortalized brain pericytes on the other surface of the porous membrane, until both of the cells become a sheet;
(b) a step of culturing conditionally immortalized brain microvascular endothelial cells in a culture vessel, until the cells become a sheet;
(c) a step of peeling off the sheet of conditionally immortalized brain microvascular endothelial cells produced in the step (b);
(d) a step of allowing the sheet of conditionally immortalized brain microvascular endothelial cells produced in the step (c) to come into contact with the sheet of conditionally immortalized brain pericytes cultured in the step (a), so that the sheets are arranged in layers; and
(e) a step of co-culturing a cell culture comprising three layers consisting of the sheet of conditionally immortalized brain microvascular endothelial cells, the sheet of conditionally immortalized brain pericytes, and the sheet of conditionally immortalized astrocytes, which are produced in the step (d).
(2) The method for producing an in vitro model for blood-brain barrier according to the above (1), wherein the culture surface of the culture vessel in the step (b) is coated with laminin, the sheet of conditionally immortalized brain microvascular endothelial cells, together with a laminin layer, is peeled off in the step (c), and the step (d) is a step of allowing the sheet of conditionally immortalized brain microvascular endothelial cells and the laminin layer produced in the step (c) to come into contact with the sheet of conditionally immortalized brain pericytes cultured in the step (a), so that they are arranged in layers.
(3) The method for producing an in vitro model for blood-brain barrier according to the above (1) or (2), wherein the conditionally immortalized brain microvascular endothelial cells, the conditionally immortalized brain pericytes, and the conditionally immortalized astrocytes are produced by introducing a temperature-sensitive SV40 large T antigen gene into primary cultured brain microvascular endothelial cells, primary cultured brain pericytes, and primary cultured astrocytes, respectively.
(4) The method for producing an in vitro model for blood-brain barrier according to any one of the above (1) to (3), wherein, in the step (b), the conditionally immortalized brain microvascular endothelial cells are cultured in a temperature-responsive culture vessel.
(5) An in vitro model for blood-brain barrier, in which a sheet of conditionally immortalized astrocytes, a porous membrane, a sheet of conditionally immortalized brain pericytes, and a sheet of conditionally immortalized brain microvascular endothelial cells are laminated in this order from the bottom, or a sheet of conditionally immortalized microvascular endothelial cells, a sheet of conditionally immortalized brain pericytes, a porous membrane, and a sheet of conditionally immortalized astrocytes are laminated in this order from the bottom.
(6) An in vitro model for blood-brain barrier, in which a sheet of conditionally immortalized astrocytes, a porous membrane, a sheet of conditionally immortalized brain pericytes, a laminin layer, and a sheet of conditionally immortalized brain microvascular endothelial cells are laminated in this order from the bottom, or a sheet of conditionally immortalized microvascular endothelial cells, a laminin layer, a sheet of conditionally immortalized brain pericytes, a porous membrane, and a sheet of conditionally immortalized astrocytes are laminated in this order from the bottom.
(7) The in vitro model for blood-brain barrier according to the above (5) or (6), wherein the conditionally immortalized brain microvascular endothelial cells, the conditionally immortalized brain pericytes, and the conditionally immortalized astrocytes are produced by introducing a temperature-sensitive SV40 large T antigen gene into primary cultured brain microvascular endothelial cells, primary cultured brain pericytes, and primary cultured astrocytes, respectively.

Advantageous Effects of Invention

According to the present invention, it becomes possible to produce an in vitro model for blood-brain barrier, in which three types of cell layers consisting of vascular endothelial cells, pericytes, and astrocytes (wherein each cell layer is formed with a single type of cells) form a layer structure in a state in which the three types of cells can directly interact with one another.

According to the present invention, it becomes possible to construct a novel in vitro model for blood-brain barrier, which has low material permeation properties and barrier function that lasts for a long period of time, when compared with known in vitro models for blood-brain barrier.

The in vitro model for blood-brain barrier according to the present invention more precisely reconstructs the anatomical structure of BBB in vivo, in comparison to known models. Accordingly, using the model of the present invention, it becomes possible to evaluate the material permeation properties of BBB, etc., in an environment close to in vivo movements.

BRIEF DESCRIPTION OF DRAWINGS

FIG. 1 is a view schematically showing an example of the in vitro model for blood-brain barrier according to the present invention.

FIG. 2 shows a microscopic image of a cell sheet of human-derived temperature-sensitive immortalized BMECs.

FIG. 3 is a view showing procedures for allowing a cell sheet of human-derived temperature-sensitive immortalized BMECs to come into contact with a cell sheet of pericytes, so that the cell sheets are arranged in layers.

FIG. 4 includes confocal microscopic images of the in vitro model for blood-brain barrier according to the present invention. (a) shows a longitudinal section of the BBB model, (b) shows a transverse section of a vascular endothelial cell layer of the BBB model, (c) shows a transverse section of a pericyte layer of the BBB model, and (d) shows a transverse section of an astrocyte layer of the BBB model.

FIG. 5 shows evaluation of the barrier function of the in vitro model for blood-brain barrier according to the present invention. EC: vascular endothelial cells; PCT: pericytes; and AST: astrocytes.

FIG. 6 is a view showing procedures for producing an in vitro model for blood-brain barrier comprising a laminin layer.

FIG. 7 shows the results obtained by evaluating the barrier function of an in vitro model for blood-brain barrier comprising a laminin layer.

DESCRIPTION OF EMBODIMENTS

A first embodiment of the present invention relates to a method for producing an in vitro model for blood-brain barrier, comprising the following steps (a) to (e):

(a) a step of culturing conditionally immortalized astrocytes on one surface of a porous membrane and culturing conditionally immortalized brain pericytes on the other surface of the porous membrane, until both of the cells become a sheet;
(b) a step of culturing conditionally immortalized brain microvascular endothelial cells in a culture vessel, until the cells become a sheet;
(c) a step of peeling off the sheet of conditionally immortalized brain microvascular endothelial cells produced in the step (b);
(d) a step of allowing the sheet of conditionally immortalized brain microvascular endothelial cells produced in the step (c) to come into contact with the sheet of conditionally immortalized brain pericytes cultured in the step (a), so that the sheets are arranged in layers; and
(e) a step of co-culturing a cell culture comprising three layers consisting of the sheet of conditionally immortalized brain microvascular endothelial cells, the sheet of conditionally immortalized brain pericytes, and the sheet of conditionally immortalized astrocytes, which are produced in the step (d).

In the first embodiment of the present invention, the "conditional immortalization" means characteristics of cells, in which a mutation treatment, an exogenous gene, etc. is introduced into primary cultured cells of each of astrocytes, brain pericytes (brain-derived pericytes), and brain microvascular endothelial cells (brain microvessel-derived vascular endothelial cells), and then, if cell culture is carried out under certain conditions, cell growth (immortalization) is induced, but if cell culture is carried out under other conditions, such cell growth is terminated and differentiation into mature cells is promoted. More specifically, examples of the "conditionally immortalized" cells that can be preferably used in the embodiment of the present invention include temperature conditionally immortalized astrocytes, temperature conditionally immortalized brain pericytes, and temperature conditionally immortalized brain microvascular endothelial cells, in which the cell growth is induced and the cells are immortalized under certain temperature conditions, whereas the cell growth is terminated and differentiation of the cells is promoted.

Examples of such temperature conditionally immortalized cells include, but are not limited to, primary culture cells (primary cultured astrocytes, primary cultured brain pericytes, and primary cultured brain microvascular endothelial cells), into which a temperature-sensitive SV 40 large T antigen gene has been introduced. The temperature-sensitive SV 40 large T antigen binds to p53 and Rb proteins as strong tumor suppressor genes and inhibits their functions in a cell that is cultured at about 33° C. Consequently, the temperature-sensitive SV 40 large T antigen induces continuous cell growth. The methods for producing temperature conditionally immortalized astrocytes, temperature conditionally immortalized brain pericytes, and temperature conditionally immortalized brain microvascular endothelial cells are described in detail in Haruki et al., J Neurological Science 331 136-144 2013; Shimizu et al., J Cell Physiol 226 255-266 2010; and Sano et al., J Cell Physiol 225 519-528 2010, respectively. So, please refer to these publications.

In the step of culturing the conditionally immortalized cells produced using the temperature-sensitive SV 40 large T antigen, until the cells become a sheet (for example, the above-described step (a) or (b)), the culture temperature may be set at 32° C. to 34° C., and preferably at 33° C. In addition, the culture temperature applied upon the co-culture of a vascular endothelial cell sheet, a pericyte sheet, and an astrocyte sheet may be set at 35° C. to 38° C., and preferably at 37° C.

It is to be noted that individual primary culture cells may be prepared by a person skilled in the art according to a publicly known method.

When in vivo BBB is reconstructed in vitro, a structure consisting of three layers, namely, a vascular endothelial cell layer, a pericyte layer, and an astrocyte layer, needs to be constructed. However, when a multi-culture model for BBB has intended to be produced according to an ordinary dispersion culture method, using three types of cultured cell lines consisting of vascular endothelial cells, pericytes, and astrocytes, since the three cell lines have different growth rates from one another, each cell line has not formed a structure consisting of a single type of cell layer, and thus, an anatomical structure, in which the three types of cells formed a three-layer structure, could not be reconstructed.

Hence, the present inventors have cultured pericytes and astrocytes on both surface of a porous membrane, until the cells have each become a sheet, and at the same time, have cultured vascular endothelial cells, separately, in a culture vessel, etc., until the cells have become a sheet. Thereafter, the present inventors have allowed a sheet (cell layer) of pericytes to come into contact with a sheet (cell layer) of vascular endothelial cells, so that the sheets are arranged in layers, and the three types of cell layers have been then co-cultured. As a result, the present inventors have succeeded in constructing a BBB model as schematically shown in FIG. 1.

The culture of each type of cells may be carried out, until what is called a "cell sheet" is formed (wherein the "cell sheet" means a cell culture in which cells bind to one another in the form of a sheet, and the cell sheet may be either a single layer or multiple layers, and is preferably a single layer). The cells may be cultured until the cell density becomes over-confluent (which is a state in which the cell density is slightly higher than a confluent state), for example, $1.0 \times 10^6$ cells/cm-$^2$ to $2.0 \times 10^6$ cells/cm-$^2$, and preferably approximately $1.5 \times 10^6$ cells/cm-$^2$.

In the step (a) of the first embodiment of the present invention, conditionally immortalized astrocytes are cultured on one surface of a porous membrane, and conditionally immortalized brain pericytes are cultured on the other surface of the porous membrane, so that a sheet-like cell layer (cell sheet) consisting of each type of cells is formed.

Herein, a porous membrane, which can be used in a state in which the porous membrane is immersed in a culture solution such that it does not directly contact with the bottom of a culture vessel, as shown in FIG. 1, is preferably used. As such a porous membrane and culture vessel, it is also possible to obtain commercially available products (for example, a cell culture insert (the bottom surface of which consists of a porous membrane) and a culture vessel, which are provided by Corning International, Thermo Scientific, Greiner Bio-One International, etc.).

The porous membrane used in the embodiment of the present invention has a large number of pores. The in vitro model for blood-brain barrier according to the present invention can be used to evaluate the BBB permeability of a substance acting on the central nervous system or a substance affecting the central nervous system. Thus, the porous membrane needs to have pores with a pore size necessary for permeation of various types of substances, etc., for examples, pores having a diameter of approximately 0.4 µm to 8 µm. The pore size can be selected, as appropriate, depending on the size of a substance to be evaluated in terms of permeability through the blood-brain barrier, etc., using the BBB model of the present invention. Differing from conventional models (for example, the model disclosed in Patent Literature 2, etc.), in the BBB model of the present invention, pericytes can directly interact with astrocytes via a porous membrane. The direct interaction of astrocytes with pericytes is possible, if the pore size of the porous membrane is, for example, a diameter of 0.4 μm or more.

The step (b) of the first embodiment of the present invention is a step of culturing conditionally immortalized brain microvascular endothelial cells in a culture vessel, until the cells become a sheet.

The culture vessel used to culture a cell sheet of conditionally immortalized brain microvascular endothelial cells may be a commonly used culture vessel. The type of the culture vessel is not particularly limited, as long as the cells can form a cell sheet on the surface thereof. Such a culture vessel is equipped with, at least, a flat portion to which cells can adhere, and it is typically a cell culture dish or a cell culture bottle (or flask). A commercially available culture dish and the like can be used, and a material for the culture vessel is not particularly limited, either. Examples of such a material for the culture vessel include polyethylene, polypropylene, and polyethylene terephthalate.

Moreover, the culture vessel may be produced with a material, the physical properties of the culture surface of which are changed depending on a temperature change and the like (temperature-responsive material), or the culture vessel may also be a temperature-responsive culture vessel, the culture surface of which is coated with a temperature-responsive material in a layer state. Such a temperature-responsive culture vessel has a hydrophobic culture surface at an ordinary culture temperature (e.g., 20° C. or higher), and thus, the cells can stably adhere onto the surface. As the temperature is decreased (e.g., a temperature lower than 20° C.), the culture surface of the temperature-responsive culture vessel becomes hydrophilic, and as a result, the cells can be easily recovered in the state of a sheet, while retaining the extracellular matrix, without performing special treatments (e.g., a trypsin treatment). As such a temperature-responsive culture vessel, a commercially available product can be obtained and used.

On the culture surface of a culture vessel, cell adhesion components and/or cell adhesion inhibitory components may be present. The type of such a cell adhesion component is not particularly limited, as long as it is a component that is commonly used in adhesion of cells onto the culture surface in cell culture technology. Examples of such a cell adhesion component include collage, fibronectin, laminin, heparan sulfate proteoglycan, cadherin, gelatin, fibrinogen, fibrin, poly-L-lysine, hyaluronic acid, platelet-rich plasma, and polyvinyl alcohol. Also, the type of a cell adhesion inhibitory component is not particularly limited, as long as it is a component that is commonly used to inhibit adhesion of cells onto the culture surface in cell culture technology. Examples of such a cell adhesion inhibitory component include albumin and globulin. A solution containing the aforementioned component, which is used in the coating of the culture surface, has each different concentration, depending on the type of the component. Accordingly, when the culture surface of a cell culture vessel is coated with such a component, the concentration of a solution containing the component, which is suitable for the coating of the culture surface with the component, can be determined by a method easily studied by a person skilled in the art, such as a preliminary experiment.

Among others, laminin is a main component of a basement membrane that is one constitutional element of a blood-brain barrier (see, for example, Takeshita et al., Clinical and Experimental Neuroimmunology 8: 49-53 2017, etc.). As such, a cell sheet of conditionally immortalized brain microvascular endothelial cells is produced in a laminin-coated culture vessel, and thereafter, when the cell sheet is peeled off (step (c)), it is peeled off together with the laminin layer (i.e., laminin adhering to the cells in the cell sheet is peeled off in the form of a layer), so that an in vitro model for blood-brain barrier comprising a laminin layer may be produced. Laminin is a protein having a heterotrimeric structure constituted with three subunits, namely, subunit α, subunit β, and subunit γ. The subunit α has isoforms α1, α2, α3, α4 and α5; the subunit β has isoforms β1, β2, β3, and β4; and the subunit γ has isoforms γ1, γ2, and γ3. The laminin used in the present embodiment may have a constitution in which any isoforms of the subunits α, β and γ are combined with one another. Particularly preferably, it is a constitution of α4β1γ1 and/or α5β1γ1. The culture surface of a culture vessel can be easily coated with laminin according to a known technique. For instance, desired laminin is diluted with a suitable buffer, the thus diluted laminin is then added (or applied) to a culture surface, and the culture surface is then left at rest, so that the culture surface can be coated with laminin.

Besides, various types of laminin products are commercially available (for example, Biolamina), and such commercially available products can be purchased and used.

In the step (c) of the first embodiment of the present invention, when a cell sheet of conditionally immortalized brain microvascular endothelial cells is peeled off from the culture vessel, it is preferably carried out by a method that does not damage the sheet-like structure. For example, physical methods, such as a method of directly pinching the cell sheet with a pair of forceps and then peeling it off from the culture surface, or a method of peeling the cells from the culture surface by pipetting, may be applied.

More preferably, a cell sheet of conditionally immortalized brain microvascular endothelial cells is formed in the aforementioned temperature-responsive culture vessel, and thereafter, the temperature is adjusted to a temperature at which the cells can be easily peeled off from the temperature-responsive culture vessel, such as 20° C. or lower, so as to create a state in which the cell sheet can be easily peeled off from the culture vessel, thereby peeling off the cell sheet. In particular, in the case of peeling off the cell sheet together with a laminin layer, the cell sheet can be easily peeled off by using such a temperature-responsive culture vessel.

Such an easily peelable cell sheet can be peeled off with a pair of forceps, etc. However, the cells can also be peeled off and recovered, for example, by covering the upper surface of the cell sheet with a water-absorbable supporting film (e.g., a base material consisting of a material having affinity for cells, such as a PVDF film or a nitrocellulose film), and then moving the cells to the film. In the case of using such a water-absorbable supporting film, the water-absorbable supporting film is laminated on a cell sheet of brain microvascular endothelial cells, it is then left at rest at 20° C. to 25° C. for several minutes (approximately 1 to 10 minutes), so that the cell sheet is allowed to adhere to the water-absorbable supporting film. Thereafter, the supporting film is slowly lifted up, so that the cell sheet can be peeled off from the culture vessel in a state in which the cell sheet still adheres to the supporting film. Since such a water-absorbable supporting film is commercially available, a commercially available product can be purchased, and then, the cell sheet can be moved to the purchased supporting film in accordance with an instruction manual included therewith.

The step (d) of the first embodiment of the present invention is a step of allowing the cell sheet of brain microvascular endothelial cells produced in the step (c) to come into contact with the cell sheet of brain pericytes cultured in the step (a), so that the cell sheets are arranged in layers. Otherwise, the step (d) is a step of allowing the cell sheet of conditionally immortalized brain microvascular endothelial cells and the laminin layer produced in the step (c) to come into contact with the sheet of conditionally immortalized brain pericytes cultured in the step (a), so that they are arranged in layers. In this case, the laminin layer is allowed to come into contact with the cell sheet of conditionally immortalized brain pericytes.

The phrase "be allowed to come into contact with . . . , so that the sheets are arranged in layers" means that a cell sheet of brain pericytes is allowed to come into contact with a cell sheet of brain microvascular endothelial cells, so that the two cell sheets are overlapped with each other. For example, in a case where a sheet of brain microvascular endothelial cells is peeled off using a water-absorbable supporting film in the step (c), the surface of the cell sheet is allowed to come into contact with the surface of the cell sheet of brain pericytes, the cell sheets are then left at rest for a while (e.g., at approximately 20° C. to 25° C. for approximately 1 to 5 minutes), and thereafter, the water-absorbable supporting film is slowly peeled off from the cell sheets, so that the step (d) can be implemented.

The step (e) of the first embodiment of the present invention is a step of co-culturing a cell culture comprising three layers consisting of the sheet of conditionally immortalized brain microvascular endothelial cells, the sheet of conditionally immortalized brain pericytes, and the sheet of conditionally immortalized astrocytes, which are produced in the step (d) of the first embodiment of the present invention.

In this step, the cell culture forms a layer structure, in which, for example, a sheet of astrocytes, a porous membrane, a sheet of brain pericytes, and a sheet of brain microvascular endothelial cells are laminated in this order from the bottom, as shown in FIG. 1. Alternatively, in a case where the brain microvascular endothelial cell sheet is peeled off together with a laminin layer, the cell culture forms a layer structure, in which a sheet of astrocytes, a porous membrane, a sheet of brain pericytes, a laminin layer, and a sheet of brain microvascular endothelial cells are laminated in this order from the bottom, as shown in FIG. 6. In the present embodiment, in a case where cells, into which a temperature-sensitive SV 40 large T antigen has been introduced, are used as conditionally immortalized cells, after the formation of a three-layer structure of cells, the culture temperature may be set at 35° C. to 38° C., and preferably at approximately 37° C., in order to terminate the growth of the cells and promote the differentiation thereof.

A second embodiment of the present invention relates to an in vitro model for blood-brain barrier, which is characterized in that a sheet of conditionally immortalized astrocytes, a porous membrane, a sheet of conditionally immortalized brain pericytes, and a sheet of conditionally immortalized brain microvascular endothelial cells are laminated in this order from the bottom (see FIG. 1), or in that a sheet of conditionally immortalized microvascular endothelial cells, a sheet of conditionally immortalized brain pericytes, a porous membrane, and a sheet of conditionally immortalized astrocytes are laminated in this order from the bottom. Otherwise, in a case where a brain microvascular endothelial cell sheet is peeled off together with a laminin layer, the second embodiment of the present invention relates to an in vitro model for blood-brain barrier, which is characterized in that a sheet of conditionally immortalized astrocytes, a porous membrane, a sheet of conditionally immortalized brain pericytes, a laminin layer, and a sheet of conditionally immortalized brain microvascular endothelial cells are laminated in this order from the bottom (see FIG. 6), or in that a sheet of conditionally immortalized microvascular endothelial cells, a laminin layer, a sheet of conditionally immortalized brain pericytes, a porous membrane, and a sheet of conditionally immortalized astrocytes are laminated in this order from the bottom.

The in vitro model for blood-brain barrier according to the present embodiment can be used for the purpose of evaluating the drug permeation properties of a blood-brain barrier, etc. For instance, a drug to be evaluated is added into a culture solution in the upper portion of a porous membrane, and thereafter, the degree of the drug detected in a culture solution in the lower portion of the porous membrane is examined, so that the permeability of the drug through the blood-brain barrier can be evaluated.

The disclosures of all publications cited in the present description are incorporated herein by reference in their entirety. In addition, when singular terms with the article "a," "an," and "the" are used throughout the present description, these terms indicate not only singular items but also plural items, unless otherwise specified from the context.

Hereinafter, the present invention will be described in more detail in the following example. However, the present example is merely one example of the embodiments of the present invention, and therefore, it does not intend to limit the scope of the present invention.

Example

1. Experimental Methods
1-1. Production of Human-Derived Temperature-Sensitive Immortalized Astrocyte Cell Sheet On the lower surface of a collagen-coated Transwell cell culture insert (pore size: 3 μm; manufactured by coming International), human-derived temperature-sensitive astrocytes were cultured in a DMEM medium supplemented with 10% FBS under conditions of 33° C. and 5% $CO_2$, until the cells became over-confluent ($150 \times 10^4/cm^2$), so as to produce a cell sheet of human-derived temperature-sensitive immortalized astrocytes. For the subsequent observation under a confocal microscope, the human-derived temperature-sensitive astrocytes had previously been subjected to living staining with CellTracker Red™.

The above-described human-derived temperature-sensitive immortalized astrocytes were produced according to the method described in the publication (Haruki H et al., J. Neurological Science 331 (2013) 136-144). Briefly speaking, the human-derived temperature-sensitive immortalized astrocytes were produced by introducing a retrovirus vector containing a temperature-sensitive SV-40 large T antigen (tsA58) into a primary cultured strain of astrocytes obtained by isolation culture from human BBB. The temperature-sensitive SV-40 large T antigen is characterized in that it is expressed in cells and immortalizes the cells under culture conditions of 33° C., whereas it loses metabolism under culture conditions of 37° C. and as a result, immortalization of the cells is not induced but the cells are differentiated into mature cells. Accordingly, in the case of the human-derived temperature-sensitive immortalized astrocyte strain, the cells grow as immortalized cells under culture conditions of 33° C., whereas the cells do not grow under culture conditions of 37° C. but are differentiated into astrocytes.

1-2. Production of Human-Derived Temperature-Sensitive Immortalized Pericyte Sheet On the upper surface of the cell culture insert used to produce the aforementioned astrocyte cell sheet, human-derived temperature-sensitive endoneurium microvessel-derived vascular pericytes (human-derived temperature-sensitive pericytes) were cultured in a DMEM medium supplemented with 10% FBS under conditions of 33° C. and 5% $CO_2$, until the cells became over-confluent ($150\times10^4$/$cm^2$), so as to produce a cell sheet of human-derived temperature-sensitive immortalized pericytes. The human-derived temperature-sensitive immortalized pericytes had previously been subjected to living staining with Cell-Tracker Blue™.

The above-described human-derived temperature-sensitive immortalized pericytes were produced according to the method described in the publication (Shimizu et al., Journal of Cell physiology 226: 255-266 (2011)). Briefly speaking, the human-derived temperature-sensitive immortalized pericytes were produced by introducing a retrovirus vector containing a temperature-sensitive SV-40 large T antigen (tsA58) into a primary cultured strain of pericytes obtained by isolation culture from human BBB. The temperature-sensitive SV-40 large T antigen is characterized in that it is expressed in cells and immortalizes the cells under culture conditions of 33° C., whereas it loses metabolism under culture conditions of 37° C. and as a result, immortalization of the cells is not induced but the cells are differentiated into mature cells. Accordingly, in the case of the human-derived temperature-sensitive immortalized pericyte strain, the cells grow as immortalized cells under culture conditions of 33° C., whereas the cells do not grow under culture conditions of 37° C. but are differentiated into pericytes.

1-3. Production of Cell Sheet of Human-Derived Temperature-Sensitive Immortalized BMECs (Brain Microvascular Endothelial Cells)

UpCell (registered trademark; CellSeed Inc.) used as a temperature-responsive culture dish was coated with collagen, and thereafter, human-derived temperature-sensitive immortalized brain microvascular endothelial cells (human-derived temperature-sensitive immortalized BMECs: TYO8), which had been subjected to living staining with CellTracker Green™, were seeded thereon. The cells were cultured in an EGM-2 Bulletkit medium (Lonza) supplemented with 20% FBS under conditions of 33° C. and 5% $CO_2$, until the cells became over-confluent ($150\times10^4$/$cm^2$), so as to produce a cell sheet of human-derived temperature-sensitive immortalized BMECs. A photograph of the produced cell sheet of human-derived temperature-sensitive immortalized BMECs is shown in FIG. 2.

On the other hand, when a temperature-responsive culture dish was coated with laminin, the coating was carried out as follows. Human recombinant laminin α4, β1, γ1 (laminin 411: a mixture of α4, β1 and γ1) (Biolamina) and/or laminin α5, β1, γ1 (laminin 511: a mixture of α5, β1 and γ1) (Biolamina), which had been diluted with Dulbecco's PBS (DPBS) to 10 μg/ml, were added in a concentration of 1.0 μg/$cm^2$ to the UpCell dish, and were then incubated at 4° C. overnight, so that the culture dish was coated with laminin. Thereafter, human-derived temperature-sensitive immortalized BMECs were seeded on the laminin-coated UpCell dish, and were then cultured in an EGM-2 Bulletkit medium (Lonza) supplemented with 20% FBS under conditions of 33° C. and 5% $CO_2$, until the cells became over-confluent ($150\times10^4$/$cm^2$), so as to produce a cell sheet of human-derived temperature-sensitive immortalized BMECs.

The above-described human-derived temperature-sensitive immortalized BMECs were produced according to the method described in the publication (Sano Y et al., J. Cell Physiol 225: 519-528 (2010)). Briefly speaking, the human-derived temperature-sensitive immortalized BMECs were produced by introducing a vector containing the above-described temperature-sensitive SV-40 large T antigen (tsA58) into a primary cultured strain of brain microvascular endothelial cells (BMECs) obtained by isolation culture from human BBB. The human-derived temperature-sensitive immortalized BMECs grow as immortalized cells under culture conditions at 33° C., whereas the cells do not grow under culture conditions at 37° C. but are differentiated into vascular endothelial cells.

Besides, UpCell is coated with a temperature-responsive polymer and has the property of turning from hydrophobicity to hydrophilicity at a temperature of 20° C. or lower. When the cells are cultured on this polymer-coated UpCell and the temperature is then decreased to 20° C., the polymer is converted to hydrophilicity, so that the cells can be released from the culture dish and thereby, sheet-like cultured cells (in the case of coating with laminin, sheet-like cells and a laminin layer) can be recovered, while maintaining the structure and function of the cells.

1-4. Transferring of Cell Sheet of Human-Derived Temperature-Sensitive Immortalized BMECs The temperature-responsive culture dish, which had been used to produce the cell sheet of human-derived temperature-sensitive immortalized BMECs, was cooled to 20° C. Thereafter, CellShifter (manufactured by CellSeed Inc.) used as a water-absorbable supporting film was laminated on the produced human-derived temperature-sensitive immortalized BMEC cell sheet, and was then left at rest at 20° C. to 25° C. for 5 minutes, so that CellShifter was allowed to adhere to the human-derived temperature-sensitive immortalized BMEC cell sheet. Subsequently, CellShifter was slowly lifted up with a pair of forceps, so that the human-derived temperature-sensitive immortalized BMEC cell sheet was recovered. When the cell sheet was produced on a laminin-coated culture dish, the human-derived temperature-sensitive immortalized BMEC cell sheet, together with a laminin layer, could be recovered by the same operation as described above.

As shown in FIG. 3, the recovered human-derived temperature-sensitive immortalized BMEC cell sheet was transferred on the human-derived temperature-sensitive immortalized pericyte cell sheet produced in the above 1-2, so that the two cell sheets were allowed to come into contact with each other in layers. On the other hand, in the case of the human-derived temperature-sensitive immortalized BMEC cell sheet recovered together with a laminin layer, the human-derived temperature-sensitive immortalized BMEC cell sheet was transferred on the human-derived temperature-sensitive immortalized pericyte cell sheet, so that the laminin layer was allowed to come into contact with the human-derived temperature-sensitive immortalized pericyte cell sheet in layers. After completion of the transcription, the resultant was left at rest at 20° C. for 1 minute, and thereafter, a DMEM medium supplemented with 250 μl of 10% FBS was added dropwise onto CellShifter. After that, CellShifter was pinched with a pair of forceps and was then peeled off from the human-derived temperature-sensitive immortalized BMEC cell sheet. No human-derived temperature-sensitive immortalized BMECs remained in the peeled CellShifter. The thus obtained BBB model consisting of a three-layer structure of a human-derived temperature-sensitive immortalized BMEC cell sheet, a human-derived temperature-sensitive immortalized pericyte cell sheet and a human-derived temperature-sensitive immortalized astrocyte cell sheet was co-cultured at 37° C., so that cell growth was suppressed, and at the same time, the cells were differentiated and matured into vascular endothelial cells, pericytes, and astrocytes. In the after-mentioned observation of a BBB model under a confocal microscope and evaluation of the barrier function, the produced in vitro BBB model was co-cultured at 37° C. for 5 days, and was then used.

2. Results 2-1. Observation of BBB Model Under Confocal Microscope

The produced in vitro BBB model was observed under a confocal microscope (Leica SP5 laser scanning confocal microscope (Leica Wetzlar)) and a 3D image thereof was produced. The results are shown in FIG. 4. In FIG. 4, (a) is a cross-sectional photograph of three layers, and four photographs (b) to (e) are cross-sectional photographs of a vascular endothelial cell layer, a pericyte layer and an astrocyte layer, respectively. As shown in FIG. 4(a) to (e), it was confirmed that the produced in vitro BBB model had a three-layer structure, and that some astrocytes were allowed to directly come into contact not only with pericytes, but also with vascular endothelial cells (BMECSs) (for example, in the cross-section of the pericyte layer shown in FIG. 4(c), some vascular endothelial cells and some astrocytes are observed, and thus, it is shown that astrocytes were allowed to come into contact not only with pericytes, but also with vascular endothelial cells).

From the aforementioned observation results, it became clear that the BBB in vitro model according to the present invention has the anatomical characteristics of BBB that the in vitro model has a three-layer structure of a layer of BMECs (brain-derived vascular endothelial cells), a pericyte layer and an astrocyte layer, while sandwiching a porous membrane therein, and that the astrocytes directly interact with the pericytes and the BMECs (brain-derived vascular endothelial cells).

2-2. Evaluation of Barrier Function

Using the BBB in vitro model (EC/PCT/AST) produced herein and another in vitro BBB model produced by a conventional method (EC/PCT-AST: a model, in which a human-derived temperature-sensitive immortalized BMEC cell sheet is formed on the upper surface of a cell culture insert, a pericyte cell sheet is formed on the lower surface thereof, and further, astrocytes are cultured on a well located 10 mm downward of the cell culture insert), FITC-added 10K-dextran was administered onto the upper surface of the insert, and 60 minutes after the administration, the absorbance ($OD_{459}$) of dextran permeating into the well was measured, followed by comparison of cell permeation properties.

The conventional BBB in vitro model was produced according to the method described in Non Patent Literature 1. Briefly speaking, human-derived temperature-sensitive immortalized pericytes were seeded on the lower surface of a collagen-coated Transwell cell culture insert (pore size: 3 μm manufactured by Corning International) and were then cultured. Thereafter, human-derived temperature-sensitive immortalized BMECs were seeded on the upper surface thereof and were then cultured. Moreover, human-derived temperature-sensitive immortalized astrocytes were seeded on a well and were then cultured, thereby producing a BBB in vitro model. The results are shown in FIG. 5.

As shown in FIG. 5, it became clear that cell permeation properties were significantly decreased in the BBB in vitro model of the present invention, than in the conventional BBB in vitro model. These results demonstrated that the BBB in vitro model of the present invention has higher barrier function than the conventional BBB in vitro model. Moreover, since the conventional BBB in vitro model was produced using temperature-non-sensitive immortalized cells, it resulted in over-culture two days after the production of the model, the barrier function was decreased, and thereby, it was difficult to evaluate the barrier function. On the other hand, since the present BBB model was produced using a temperature-sensitive immortalized cell line, it has the properties that immortalization of the cells was suspended by a change in the culture temperature from 33° C. to 37° C., and are differentiated into mature cells. It has been clarified that the present BBB model maintains its barrier function even 5 days after the co-culture. Accordingly, it became clear that the barrier function can be evaluated, while adding various conditions, such as evaluation of the long-term action of BBB, or disease in which BBB is destructed due to the chronic course thereof.

Subsequently, using a BBB in vitro model comprising a laminin layer, FITC-added 10K-dextran was administered onto the upper surface of an insert, and 60 minutes after the administration, the absorbance ($OD_{459}$) of dextran permeating into the well was measured, followed by comparison of cell permeation properties. The results are shown in FIG. 7. A model comprising a blood-brain barrier-specific laminin layer (containing α4 or α5β1γ1), a model comprising a blood-nerve barrier-specific laminin layer (containing α4β1γ1), and a model comprising no laminin layers were compared in terms of cell permeation properties.

The fluorescence microscopy image on the right of FIG. 7 shows the results obtained by immunostaining a vascular endothelial cell layer with antibodies against Claudin-5 and Zo-1 that are constituent molecules of a tight junction. The expression levels of Claudin-5 and Zo-1 in the model comprising a blood-nerve barrier-specific laminin layer (FIG. 7, right view, middle case) were higher than the expression levels thereof in the model comprising no laminin layers (FIG. 7, right view, upper case). The expression levels of Claudin-5 and Zo-1 in the model comprising a blood-brain barrier-specific laminin layer (FIG. 7, right view, lower case) were higher than those in two other models. The graph on the left of FIG. 7 shows the results obtained by administering FITC-added 10K-dextran onto the upper surface of the insert, and 60 minutes after the administration, measuring the absorbance ($OD_{49}$) of dextran permeating into the well. The cell permeation properties were indicated as a relative value of the measured absorbance, when the absorbance of a model comprising no laminin was defined as 1. From these results, it was found that, with regard to the barrier function of the BBB in vitro model according to the present invention, the model comprising a blood-brain barrier-specific laminin layer has the most excellent barrier function, the model comprising a blood-nerve barrier-specific laminin layer has the second most excellent barrier function, and the model comprising no laminin layers has the lowest barrier function.

From the aforementioned results, it was demonstrated that the barrier function of the BBB in vitro model according to the present invention is improved by addition of a laminin layer.

INDUSTRIAL APPLICABILITY

The present invention provides a novel in vitro model for blood-brain barrier, in which three types of cell layers consisting of vascular endothelial cells, pericytes, and astrocytes form a layer structure in a state in which these cells can directly interact with one another, and the barrier function thereof is sustained for a long period of time. Accordingly, it is expected that the present invention will be utilized in a medical field, such as elucidation of the pathologic conditions of central nervous system diseases and the treatment thereof.

The invention claimed is:

1. A method for producing an in vitro model for blood-brain barrier, comprising the following steps (a) to (e):
   (a) a step of culturing conditionally immortalized astrocytes on one surface of a porous membrane and culturing conditionally immortalized brain pericytes on the other surface of the porous membrane, until both of the cells become a sheet;
   (b) a step of culturing conditionally immortalized brain microvascular endothelial cells in a temperature-responsive culture vessel, until the cells become a sheet;
   (c) a step of peeling off the sheet of conditionally immortalized brain microvascular endothelial cells produced in the step (b);
   (d) a step of allowing the sheet of conditionally immortalized brain microvascular endothelial cells produced in the step (c) to come into contact with the sheet of conditionally immortalized brain pericytes cultured in the step (a), so that the sheets are arranged in layers; and
   (e) a step of co-culturing a cell culture comprising three layers consisting of the sheet of conditionally immortalized brain microvascular endothelial cells, the sheet of conditionally immortalized brain pericytes, and the sheet of conditionally immortalized astrocytes, which are produced in the step (d),
   wherein the conditionally immortalized brain microvascular endothelial cells, the conditionally immortalized brain pericytes, and the conditionally immortalized astrocytes are produced by introducing a temperature-sensitive SV40 large T antigen gene into primary cultured brain microvascular endothelial cells, primary cultured brain pericytes, and primary cultured astrocytes, respectively.

2. The method for producing an in vitro model for blood-brain barrier according to claim 1, wherein the culture surface of the temperature-responsive culture vessel in the step (b) is coated with laminin, the sheet of conditionally immortalized brain microvascular endothelial cells, together with a laminin layer, is peeled off in the step (c), and the step (d) is a step of allowing the sheet of conditionally immortalized brain microvascular endothelial cells and the laminin layer produced in the step (c) to come into contact with the sheet of conditionally immortalized brain pericytes cultured in the step (a), so that they are arranged in layers.

3. An in vitro model for blood-brain barrier, in which a sheet of conditionally immortalized astrocytes, a porous membrane, a sheet of conditionally immortalized brain pericytes, and a sheet of conditionally immortalized brain microvascular endothelial cells are laminated in this order from the bottom, or a sheet of conditionally immortalized microvascular endothelial cells, a sheet of conditionally immortalized brain pericytes, a porous membrane, and a sheet of conditionally immortalized astrocytes are laminated in this order from the bottom,
   wherein the conditionally immortalized brain microvascular endothelial cells, the conditionally immortalized brain pericytes, and the conditionally immortalized astrocytes are produced by introducing a temperature-sensitive SV40 large T antigen gene into primary cultured brain microvascular endothelial cells, primary cultured brain pericytes, and primary cultured astrocytes, respectively.

4. An in vitro model for blood-brain barrier, in which a sheet of conditionally immortalized astrocytes, a porous membrane, a sheet of conditionally immortalized brain pericytes, a laminin layer, and a sheet of conditionally immortalized brain microvascular endothelial cells are laminated in this order from the bottom, or a sheet of conditionally immortalized microvascular endothelial cells, a laminin layer, a sheet of conditionally immortalized brain pericytes, a porous membrane, and a sheet of conditionally immortalized astrocytes are laminated in this order from the bottom,
   wherein the conditionally immortalized brain microvascular endothelial cells, the conditionally immortalized brain pericytes, and the conditionally immortalized astrocytes are produced by introducing a temperature-sensitive SV40 large T antigen gene into primary cultured brain microvascular endothelial cells, primary cultured brain pericytes, and primary cultured astrocytes, respectively.

* * * * *